(12) United States Patent
Lucas et al.

(10) Patent No.: US 10,173,151 B2
(45) Date of Patent: Jan. 8, 2019

(54) FILTER ELEMENT AND FILTRATION ASSEMBLY FOR BIOPHARMACEUTICAL APPLICATIONS

(71) Applicant: 3M INNOVATIVE PROPERTIES COMPANY, St. Paul, MN (US)

(72) Inventors: Jeffrey A. Lucas, Clinton, CT (US); Kenneth M. Burke, Cheshire, CT (US); Anna I. Bailey, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 151 days.

(21) Appl. No.: 14/909,191

(22) PCT Filed: Aug. 5, 2014

(86) PCT No.: PCT/US2014/049671
§ 371 (c)(1),
(2) Date: Feb. 1, 2016

(87) PCT Pub. No.: WO2015/023468
PCT Pub. Date: Feb. 19, 2015

(65) Prior Publication Data
US 2016/0175744 A1    Jun. 23, 2016

Related U.S. Application Data

(60) Provisional application No. 61/866,167, filed on Aug. 15, 2013.

(51) Int. Cl.
*B01D 29/05* (2006.01)
*B01D 29/01* (2006.01)
(Continued)

(52) U.S. Cl.
CPC .......... *B01D 29/05* (2013.01); *B01D 29/012* (2013.01); *B01D 29/41* (2013.01); *B01D 29/56* (2013.01);
(Continued)

(58) Field of Classification Search
CPC ...... B01D 29/05; B01D 29/56; B01D 29/012; B01D 29/41; B01D 15/125; G01M 3/02; G01N 2030/146
(Continued)

(56) References Cited

U.S. PATENT DOCUMENTS 4,039,455 A    8/1977  Bardin
4,501,663 A    2/1985  Merrill
(Continued)

FOREIGN PATENT DOCUMENTS

EP    0 672 442    9/1995
EP    1 398 065    3/2004
(Continued)

*Primary Examiner* — Madeline Gonzalez
(74) *Attorney, Agent, or Firm* — Scott A. Baum

(57) ABSTRACT

Provided are filter elements or cells and filtration assemblies or capsules for purifying and/or clarifying fluids used during various biopharmaceutical applications, for example, chromatography or depth filtration, and processes for making and using the same. A filter element comprises a media pack comprising two sides and a separator element located between the two sides, at least one side comprising a filtration media, wherein an inner edge periphery and/or an outer edge periphery of the filtration media comprise a bond directly to a portion of the separator element.

26 Claims, 7 Drawing Sheets

(51) Int. Cl.
    *G01M 3/02*     (2006.01)
    *B01D 29/56*     (2006.01)
    *B01D 29/41*     (2006.01)
    *B01D 15/12*     (2006.01)
    *G01N 30/14*     (2006.01)

(52) U.S. Cl.
    CPC ............ *G01M 3/02* (2013.01); *B01D 15/125* (2013.01); *G01N 2030/146* (2013.01)

(58) Field of Classification Search
    USPC ....... 210/232, 483, 495, 338, 317, 486, 490, 210/455, 314
    See application file for complete search history.

(56) References Cited

U.S. PATENT DOCUMENTS

| | | | |
|---|---|---|---|
| 4,637,877 A * | 1/1987 | Hartmann | B01D 29/41 |
| | | | 210/347 |
| 4,783,262 A | 11/1988 | Ostricher | |
| 4,874,513 A | 10/1989 | Chakraborty | |
| 5,011,555 A | 4/1991 | Sagar | |
| 5,443,723 A | 8/1995 | Stankowski | |
| 5,660,771 A | 8/1997 | Dunfee | |
| 6,324,898 B1 * | 12/2001 | Cote | B01D 65/102 |
| | | | 210/90 |
| 2003/0080043 A1 | 5/2003 | Renganath | |
| 2003/0094735 A1 | 5/2003 | Faulkner | |
| 2004/0118766 A1 * | 6/2004 | Pulek | B01D 29/111 |
| | | | 210/317 |
| 2005/0245884 A1 | 11/2005 | Deininger | |
| 2007/0080104 A1 | 4/2007 | Rautio | |
| 2011/0226691 A1 | 9/2011 | Lucas | |
| 2011/0244013 A1 | 10/2011 | Mrozinski | |
| 2011/0259812 A1 * | 10/2011 | Marks | B01D 29/41 |
| | | | 210/483 |

FOREIGN PATENT DOCUMENTS

| | | |
|---|---|---|
| FR | 2816876 | 5/2002 |
| JP | 63-093314 | 4/1988 |
| JP | 2012-232229 | 11/2012 |
| WO | WO 2010/053898 | 5/2010 |
| WO | WO 2013/043362 | 3/2013 |

* cited by examiner

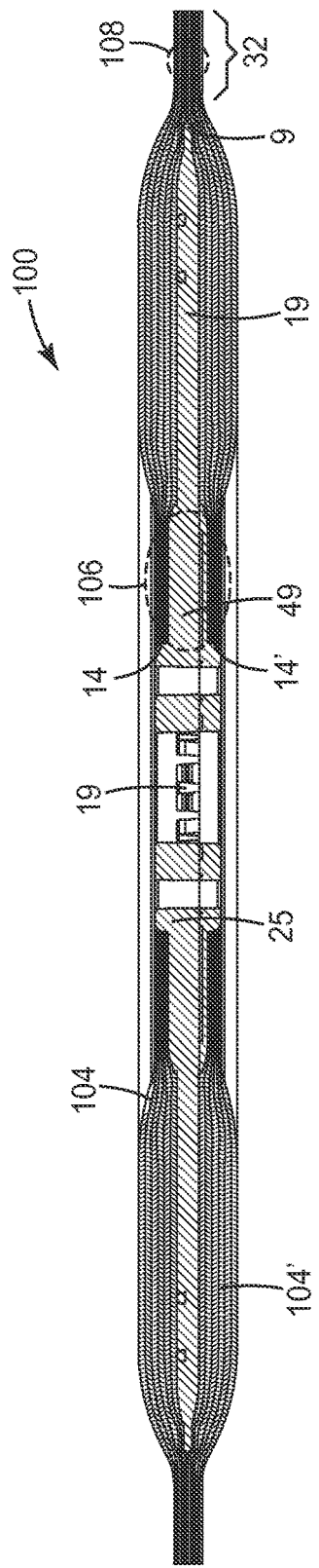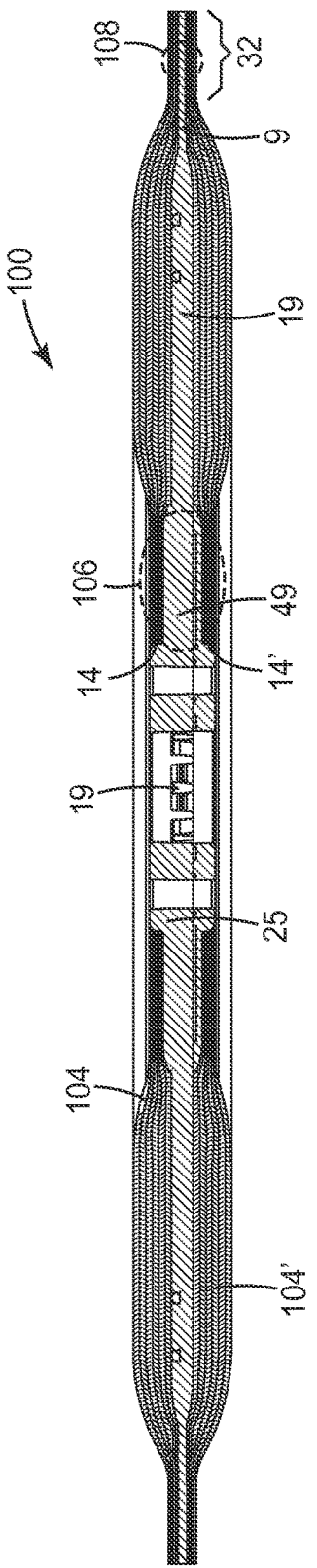

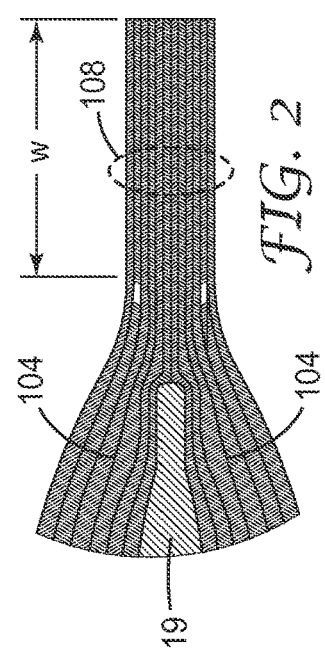
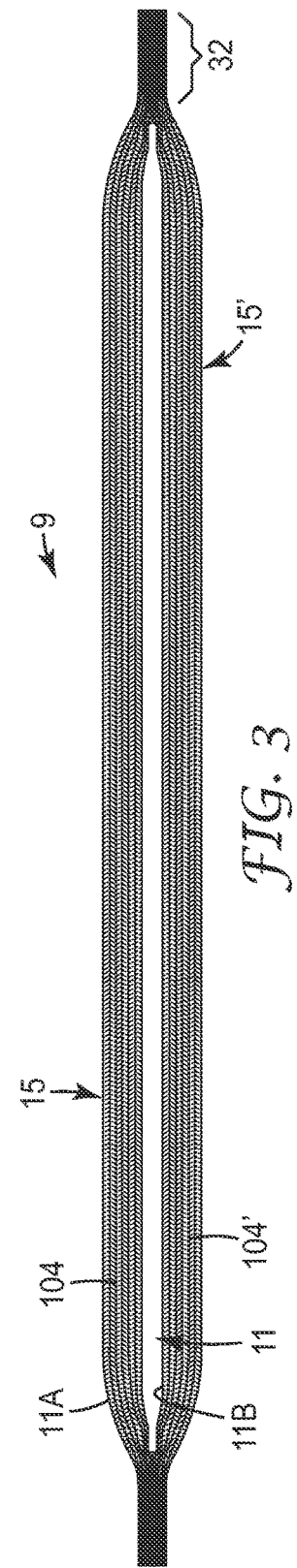

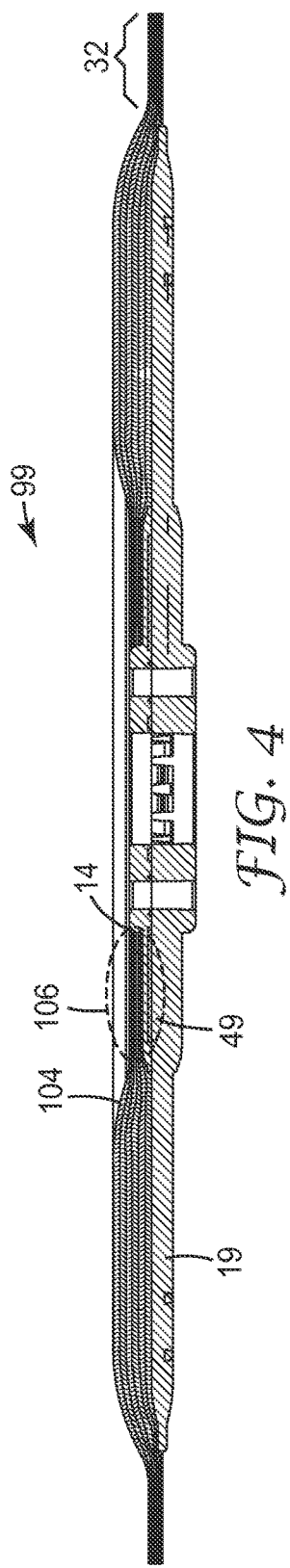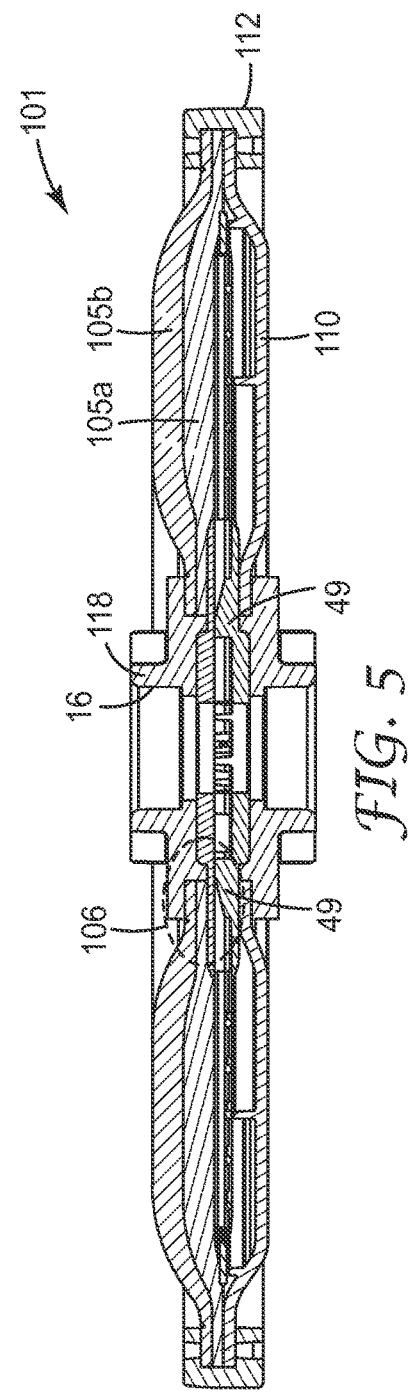

FILTER ELEMENT AND FILTRATION ASSEMBLY FOR BIOPHARMACEUTICAL APPLICATIONS

TECHNICAL FIELD

The present disclosure generally relates to the field of filter elements or cells and filtration assemblies or capsules for purifying and/or clarifying fluids used during biopharmaceutical applications, for example, in chromatography or depth filtration applications, and processes for making and using the same.

BACKGROUND

Products of bioprocesses, specifically biopharmaceuticals, are valuable. When purifying and/or analyzing such products, careful consideration and attention during all aspects of preparation are given to minimize waste and maximize yield of these products. WO2013/043362, commonly-assigned and incorporated herein by reference, discloses a filter element and filtration assembly for bioprocess applications where residual volumes are minimized. With respect to formation of filter elements or cells, WO 2010/053898, also commonly-assigned and incorporated herein by reference, discloses a filter element and seal therefor where an overmold seal at an edge of a media pack seals the media pack to a separator element There is an on-going need to provide filter elements and filtration assemblies that can minimize residual volumes and that accommodate various types of filtration media.

SUMMARY

Provided are filter element or cells and filtration assemblies or capsules for purifying fluids used during various biopharmaceutical applications, for example, chromatography or depth filtration, and processes for making and using the same.

As separation technologies improve, opportunities arise to replace cumbersome filtration techniques with simpler, less costly, and, in many instances, disposable options. It has been found that by forming filter elements/cells from one or more media layers in conjunction with a separator element, traditional packed columns used for chromatography or large stainless steel pressure vessels used for depth filtration may be replaced. With the techniques used herein, where a media layer is bonded directly to a separation element and the other media layers are bonded to each other, the following benefits are achieved: (1) filter layers are held concentric to the separator element thereby creating a flow path for process fluid; (2) a rigid outer periphery of the filter element is formed thereby allowing for subsequent over-molding as desired to further seal the outer diameter; (3) hermetic seals on inner and outer diameter of filter element are formed thereby allowing the filter element to be integrity tested; and (4) simpler, less costly, and disposable filtration cells relative to existing technologies are provided. In particular, when one or more of the media layers are formed from microporous polymeric membranes and are thin, slippery with respect to each other, and of differing materials, the techniques herein permit the formation of a filter element, full or half cell, that is easy to handle and may accommodate such characteristics.

In addition, the use of packed columns in chromatography may introduce problems including but not limited to: inconsistent filtration results due to variations in packing, high costs of capital for columns and resins, and cumbersome and lengthy cleanings needed between campaigns. The filter elements provided herein help to eliminate a need for packed columns in chromatography and other similar applications. The filter elements or cells provided herein: provide concentricity of multiple filter layers with a separator element, allow for an integral over-molded seal on an inner diameter, an outer diameter, or both; and create a structure that is able to be integrity tested.

In a first aspect, provided are filter elements comprising: a media pack comprising two sides each comprising: an inner edge having an inner edge periphery and an outer edge having an outer edge periphery, wherein at least one side comprises a filtration media; a separator element located between the two sides, the separator element comprising a central hub defining a central separator opening, a plurality of support members, and optionally, an outer lip; wherein at lease one of the inner edge periphery and the outer edge periphery comprises a bond directly to a portion of the separator element.

Other features that may be used individually or in combination are as follows. The bond may be continuous thereby forming a hermetic seal. The bond may comprise an adhesive or a weld. The bond may comprise a weld selected from the group consisting of an ultrasonic weld, a high-frequency weld, a vibration weld, a friction weld, a laser weld, a solvent weld, a contact weld, a hot plate weld, a plastic rod weld, a speed tip weld, or a hot gas weld. The bond may have a width that is in the range of 50 mil to 250 mil from at least one of the inner edge and the outer edge of the filtration media.

When the separator element comprises the outer lip, a surface of the central hub and a surface of the outer lip may be in the same plane.

The bond may comprise an inner bond between the inner edge periphery of the filtration media and a surface of the central hub, and/or an outer bond between the outer edge periphery of the filtration media and the outer lip.

The two sides of the media pack may both comprise the filtration media. When the two sides both comprise the filtration media, the bond may comprise an outer bond between the two filtration media.

Alternatively, a first side of the media pack may comprise the filtration media and a second side of the media pack may comprise a flow inhibitor.

The filtration media may comprise a microporous membrane produced from a polymeric material. The filtration media may comprise one or more layers of media. Each layer may comprise a thickness in the range of 5-40 mil. Each layer may independently comprise a polymeric material having a melting point in the range of 100° C. to 300° C.

A detailed aspect provides a filter element that comprises: a media pack comprising two sides each comprising: an inner edge having an inner edge periphery and an outer edge having an outer edge periphery, wherein a first side comprises a first filtration media and a second side comprises a second filtration media or a flow inhibitor; a separator element located between the two sides, the separator element comprising a central hub defining a central separator opening, a plurality of support members, and an outer lip; wherein the inner edge periphery of the first filtration media, and the second filtration media if present, comprises an inner bond directly to the washer; and wherein the outer edge periphery of the first filtration media, and the second filtration media if present, comprises an outer bond directly to the outer lip of the separator. The first filtration media may comprise two or more layers that are independently: a woven structure, a non-woven structure, a microporous membrane, a monolith, a melt-blown fiber (MBF) structure, or an open-cell foam formed from a material selected from the group consisting of: nylon, ethylene chlorotrifluoroethylene (ECTFE), polypropylene, polyethylene, polyvinylidene fluoride (PVDF), a polyethersulfone membrane, a polysulfone membrane, a polyester membrane, polytetrafluoroethylene (PTFE), polycarbonate, nitrocellulose, cellulose acetate, cellulose, or combinations thereof.

Another aspect is a method of integrity testing a filter element, the method comprising obtaining a filter element according to any embodiment wherein the inner bond and the outer bond are both continuous and wherein the filtration media may be wetted and dried without losing integrity; exposing an upstream side of the filter element to a test fluid to form an exposed element; and monitoring a downstream side of the filter element to detect leakage. In an embodiment, the test fluid may comprise a liquid, the method further comprising pressurizing the exposed element and the monitoring step comprises measuring pressure to detect leakage. In another embodiment, the test fluid may comprise a gas with particles entrained therein and the monitoring step comprises measuring a particle count to detect leakage.

A further aspect includes methods of filtering, the methods comprising: obtaining a filter element according to any embodiment disclosed herein, passing an incoming fluid through the filter element; and receiving a filtered fluid from the filter element.

In another aspect, a method of making a filter element comprises: obtaining a first filtration media comprising an inner edge having an inner edge periphery and an outer edge having an outer edge periphery; locating a separator element on the first filtration media; axially aligning the first filtration media and the separator element; and bonding at least one of the inner edge periphery and the outer edge periphery directly to the separator element to form a bond. The bonding step may comprise ultrasonically welding the inner edge periphery to a washer of the separator element to form an inner bond and the outer edge periphery to itself or directly to an outer lip of the separator element to form an outer bond. The method may further comprise forming an overmold inner seal over the inner bond, an overmold outer seal over the outer bond, or both.

Other aspects include: filtration assemblies comprising any filter element disclosed herein, located in a housing, and methods of forming a filtration assembly by locating any filter element disclosed herein in a housing.

These and other aspects of the invention are described in the detailed description below. In no event should the above summary be construed as a limitation on the claimed subject matter.

BRIEF DESCRIPTION OF THE DRAWINGS

The accompanying drawings are included to provide a further understanding of the invention described herein and are incorporated in and constitute a part of this specification. The drawings illustrate exemplary embodiments. Certain features may be better understood by reference to the following detailed description when considered in connection with the accompanying drawings, in which like reference numerals designate like parts throughout the figures thereof, and wherein:

FIGS. 1A and 1B are cross-sectional side views of different illustrative full-cell filter elements;

FIG. 2 is a cross-sectional, enlarged side view of an illustrative outer bond;

FIG. 3 is a cross-sectional side view of an illustrative media pack;

FIG. 4 is a cross-sectional side view of an illustrative partial filter element;

FIG. 5 is a cross-sectional side view of an illustrative half-cell filter element;

The figures are not necessarily to scale. Like numbers used in the figures refer to like components. It will be understood, however, that the use of a number to refer to a component in a given figure is not intended to limit the component in another figure labeled with the same number.

DETAILED DESCRIPTION

Figure 6:
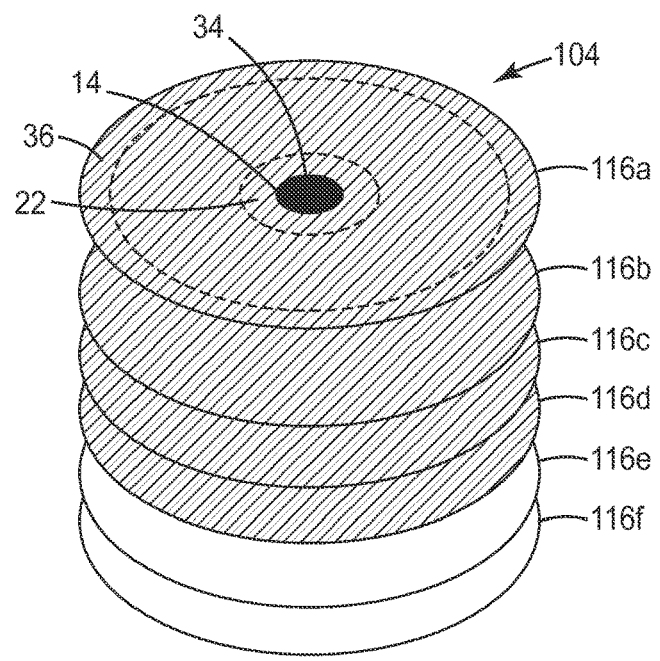
FIG. 6 is an exploded perspective schematic view of an illustrative layered filtration media.

Filter elements and filtration assemblies provided herein may be used for purifying fluids used during various biopharmaceutical applications. The following terms shall have, for the purposes of this application, the respective meanings set forth below.

Reference to a "bond" means a connection between items so that they move together as a unit. That is, media directly bonded to a structure such as a separator element does not require any compression to maintain a connection. For the purposes of this disclosure, a bond is not a structure such as an o-ring or overmold seal, but rather a connection formed by, for example, an adhesive or a weld.

A "hermetic seal" formed by, for example, a continuous bond, means that such a seal or connection is liquid and/or air tight. That is, media that is directly bonded to a structure such as a separator element with a continuous bond does not require any compression to maintain a liquid- or air-tight seal.

"Axially aligned" means that a central axis for each structure being aligned is coincident.

"Concentric" structures are structures that are axially aligned.

"Overmolding" or "overmold process" means that a seal is formed in place on a filtration media by, for example, injection molding. An overmold seal may be formed from a polymeric material (e.g., a thermoplastic material or a thermosetting material), which upon cooling or curing, as appropriate, forms a fluid-tight seal against filtration media. An overmold seal is not a bond as used herein.

It has been found that when one or more of the filtration media layers are thin, slippery with respect to each other, and of differing materials, the techniques herein permit the formation of a filter element, full or half cell, that is easy to handle and may accommodate such characteristics.

Media Pack

A media pack of the filter element comprises two sides that form an interior, at least one side is a filtration media.

The interior usually accommodates a structure such as a separator element to ensure there is space adjacent the filtration media for fluid flow. sides. While one side always comprises a filtration media, the other side may be another layer as needed, for example, another filtration media, or it may be a flow inhibitor, or perhaps even a drainage layer, depending on the application and desired filtration area. The flow inhibitor may cover and/or sealably affix to the separator element or to all or some portion of the filtration media.

Filtration Media

Examples of suitable filtration media may include cellulosic media, synthetic media, or a combination thereof. Media may have structures including, but not limited to: a woven structure, a non-woven structure, a microporous membrane, a monolith, a melt-blown fiber (MBF) structure, or an open-cell foam. In some embodiments, the filtration media may be charge modified, e.g., electrostatically treated or it may be chemically modified to provide ion exchange capacity. As desired, media may have fine fibers or nanofibers present dispersed throughout media or present as a layer thereon. The media may provide functionalities of mechanical filtration, ion exchange, and/or adsorptive capacity.

The various layers may be the same materials or differing materials. It is expected that for multi-layered configurations, more than one layer of the same material may be used in conjunction with other types of materials. The various layers are also likely different in their physical parameters such as melting point, moisture and/or wettability levels, permeability, durometry, thickness, and the like. Coefficients of friction also demonstrate the differences among various layers. In one or more examples, each layer independently comprises a polymeric material having a melting point in the range of 100° C. to 300° C. Other examples may provide that each layer comprises a thickness in the range of 1-100 mil (25.4-2540 micron) or even 5-40 mil (127-1016 micron).

Exemplary materials of construction may include, but are not limited to: nylon (e.g., nylon 6,6), ethylene chlorotrifluoroethylene (ECTFE), polypropylene, polyethylene, polyvinylidene fluoride (PVDF), polyethersulfone, polysulfone, polyester, polytetrafluoroethylene (PTFE), polycarbonate, nitrocellulose, cellulose acetate, cellulose, or combinations thereof. An exemplary membrane comprising ethylene chlorotrifluoroethylene (ECTFE) is approximately 2.0 mils thick with a minimum bubble point of 20 psi when tested with a 60/40 solution of isopropyl alchohol/water. U.S. Patent Appln. Pub. No. 2011/0244013 entitled "Microporous material from ethylene-chlorotrifluoroethylene copolymer and method for making same," commonly-assigned, discloses an exemplary ECTFE membrane and is incorporated herein by reference. Exemplary polypropylene (PP) membranes are 3M's F100 microporous polypropylene membrane (0.20 micron) and 3M's F101 microporous prolypropylene membrane 90.45 micron). Other membranes that may be considered for use include but are not limited to polyvinylidene fluoride (PVDF) membranes, polysulfone (PS) or polyethersulfone (PES) membranes, polytetrafluoroethylene (PTFE) membranes, and polyethylene (PE) membranes. In addition, surface-treated hydrophilic membranes that are rendered hydrophobic are also suitable. Other media layers that may be considered include an extruded web material, an apertured polymeric film, or combinations thereof. An exemplary extruded web material is 10 mil polypropylene Delnet (nettings). Another exemplary extruded web is 30 mil polypropylene Naltex (nettings).

Regarding open cell foams, this type of material can be purchased in a wide range of materials, pore sizes, and porosities. An example material which may be particularly useful is a polyester open cell foam with 20 pores per inch (PPI) produced by UFP Technologies of Georgetown, Mass.

A suitable porous nonwoven material may be a polypropylene nonwoven material, a polyester nonwoven material, and/or a polyethylene nonwoven material. An exemplary nonwoven material is polypropylene Typar. This type of material may assist in breaking up fluid boundary layers on adjacent media layers. This material may also provide thermoplastic material which assists in a making a good thermal weld. Typar may also provide support to other layers. Typar and Reemay materials from Fiberweb PLC are reference nonwoven materials available with a wide range of properties.

Filtration media may provide ion exchange functionality by, for example, electrically and/or chemically modifying any of the materials of construction listed above. Adsorptive capacity may be provided by adding an adsorptive material such as diatomaceous earth or activated carbon particles to any of the materials of construction listed above. Exemplary adsorptive materials include, but are not limited to cellulose impregnated with diatomaceous earth (DE), for example, a Zeta Plus™ filtration media made by 3M Purification Inc., and a carbon impregnated polypropylene meltblown fiber material.

Separator Element

Separator elements generally have a plurality of support members such as ribs, gussets, or other structures extending radially outward from a central hub in a spoke-like fashion which forms an open grid-like structure. The central hub provides a surface for defining a central separator opening. A combination of filter elements and their central hubs may form a collective passageway or core for fluid flow. Any rib geometry may be used in a separator element design to effectively maintain separation of two filtration medias of a media pack or of a filtration media and a flow inhibitor and provide a flow channel from an outer diameter or edge of the media pack to the central separator opening. Flow channels are formed by the openings between the ribs. The rib geometry may be intersected by cross-pieces in any desired configuration, such as a series of concentric rings at spaced locations in order to enhance rigidity of the separator and to facilitate flow through the channels. The combination of the central hub and the rib geometry forms passages into the central separator opening for radial fluid communication between the media pack interior and the central separator opening. The central hub may be integral to the rib geometry or it may snap-fit to it. The central hub itself may be individually-fabricated pieces or a unitary construction. For example, the central hub may comprise a washer and a center ring, where the washer provides a flange-like structure and a surface for bonding media thereto and the center ring provides through-holes for injection molding purposes. The intersection of the center ring and the washer is impermeable, which facilitates isolating the edges of filtration media from the central separator opening and, during injection molding, to contain overmold seal material until it hardens (either by cooling or curing).

Formation of Filter Elements

In order to create a filter element whose layers are concentric with a separator element, deliberate handling of the layers is needed until an inner bond on the inner diameter (ID) periphery and/or an outer bond on the outer diameter (OD) periphery has been formed to create a unit that will move and be further processed together.

Previously, in certain prior art manufacturing overmolding methods, filtration media layers were of enough weight/ substance to permit handling without creating a unit first.

That is, as an example, to form a filter element, two layers of media could be placed on a mandril, a separator element could then be placed onto the layers, and then additional layers of media could be added on top of the separator element, aligning the pieces upon addition. Upon overmolding, the materials would stay aligned because the machinery's pinch plate and teeth provided adequate compression such that the layers did not move around due to their weight/substance. When faced with filtration media of less weight/substance, that is, using thin, slippery with respect to each other, and differing materials, it has been found that using an inner bond on the inner diameter (ID) and/or an outer bond on the outer diameter (OD) to create a unit to handle solves problems such as lack of concentricity and blowby of plastic material encountered during overmolding processing. Moreover, providing a bond on the outer diameter (OD) also improves handling and solving problems encountered during overmolding.

In accordance with methods of the present invention, it was determined that securing media layers at their inner diameter (ID) and/or their outer diameter (OD) directly to the separator element would address problems identified in the prior art manufacturing. A bond at the outer diameter (OD) creates rigidity that further improves handling and consistent manufacturing of overmold seals.

Generally, the various layers of filtration media are arranged in a desired order and affixed to each other and to the separator element on the ID and/or the OD. For achieving concentricity, either a bond at the ID or OD is needed. For achieving a hermetic seal, a continuous bond at the ID is needed and sealing at the OD can be by bonding or by overmolding. With respect to bonding, at minimum, the layer of media located next to the separation element is directly bonded thereto by methods recognized in the art. For example, an adhesive or a weld may be used. As used in the present disclosure, the term "weld" means secured by any of various known polymer welding methods including, but not limited to, ultrasonic, high-frequency, vibration, friction, laser, solvent, contact, hot plate, plastic rod, speed tip, hot gas, and free hand.

In one or more embodiments, the inner and/or outer bonds are welds formed by ultrasonic methods. For ultrasonic welding, an ultrasonic horn set such as a Branson 921 AES welder with a 2000t controller may be used. Typical ultrasonic welding parameters are:

Weld pressure: 15-60 psi;
Weld Time: 0.1-4 sec;
Weld Hold Time: 1-5 sec;
Trigger Force: typically set at 12;
Down Speed: typically set at 30; and
Amplitude: typically set at 100%.

The ultrasonic welding parameters may be varied based on types of materials, thicknesses, weld surface area, melt properties of the materials, etc., in order to produce a mechanically robust, weld.

Hot wire thermal welding (impulse sealing) is another acceptable method to form a weld. Hot air welding and induction welding are additional techniques that could be applied.

Use of adhesives and/or tapes to form bonds may be desirable depending on manufacturing and application needs.

The bonds may be continuous to form a hermetic seal. Alternatively, the bonds may be discontinuous for handling purposes only. Optional additional overmold inner and/or outer seals may be used in a final assembly. Such seals may be achieved by injection molding at the proper locations of the filter element.

In one aspect, where an inner bond at the ID is desired, to manufacture the filter elements, the following steps are used: a properly-sized fixture or alignment tool is installed with respect to a mandril or other structure of a bonding device, a separator element is placed on the mandril, a first side of filtration media is placed and aligned on the separator element, the ID of the first side of filtration media is then bonded, for example, by ultrasonic welding, to the separator element to form a partial filter element. If a second side of filtration media is being used then the partial filter element is flipped over and placed on the mandril. The second side of filtration media is then placed and aligned on the partial filter element, an ID of the second side of filtration media is then bonded, for example, by ultrasonic welding, to the separator element to form a filter element with ID bonds. Should a bond at the OD be desired, and the separator element has an OD that is smaller than the OD of the filtration media, then the ODs of both the first and second filtration media may be bonded to each other at this time. Optionally, with or without an OD bond, the filter element with two ID bonds may be put into an injection molding unit to receive an overmold outer seal. If the second side is to be a flow inhibitor, then the flow inhibitor is affixed to the separator element of the partial filter element by bonding with, for example, adhesive or a weld as set forth in this disclosure.

In one another aspect, where an outer bond at the OD is desired and the separator element has an OD that is substantially the same as the OD of the filtration media, to manufacture the filter elements, the following steps are used: a properly-sized fixture or alignment tool is installed with respect to a mandril or other structure of a bonding device, a separator element is placed on the mandril, a first side of filtration media is placed and aligned on the separator element, the OD of the first side of filtration media is then bonded, for example, by ultrasonic welding, to the separator element to form a partial filter element. If a second side of filtration media is being used then the partial filter element is flipped over and placed on the mandril. The second side of filtration media is then placed and aligned on the partial filter element, an OD of the second side of filtration media is then bonded, for example, by ultrasonic welding, to the separator element to form a filter element with OD bonds. Should an overmold inner bond at the ID be desired, the filter element with two OD bonds may be put into an injection molding unit to receive an overmold inner seal. If the second side is to be a flow inhibitor, then the flow inhibitor is affixed to the separator element of the partial filter element by bonding with, for example, adhesive or a weld as set forth in this disclosure.

Integrity Testing

The filter elements disclosed herein may be integrity tested prior to their assembly into filtration capsules. Diffusion testing and aerosol challenge testing are two ways to test integrity. For diffusion testing, the media is wetted, tested, and subsequently dried. While this testing helps to eliminate any products that have media that may not be integral before it gets to the customer, it adds many additional manufacturing steps. The water used for this testing also needs to be closely regulated and maintained such that is does not introduce potential sources of bioburden to the filter.

In aerosol challenge testing, salt suspended particles flow through the upstream side of the filter. Particle count is then taken downstream and determination is made on the integrity of the product. While this test method does not require the media to be wetted to perform, it is somewhat limited at detecting small imperfections.

In practice, therefore, any of the filter elements disclosed herein having a hermetic seal at its ID and OD may be integrity tested by subjecting the filter elements to diffusion testing, aerosol challenge testing, or both.

Assembly of Filtration Capsules

In general terms, assembly of a filtration capsule involves placing one or a plurality of filter elements disclosed herein in a housing having an inlet and an outlet. A filtration cartridge may be achieved as simply as adding end adapters and seals such as o-rings to provide a dirty side upstream of the filter element and a clean side downstream of the filter element. Individual filter elements may be connected via hub assemblies, for examples. Housings may be any encapsulating shell, including but not limited to existing stainless steel vessels or plastic capsules. Filter elements may be sized as needed to fit into a desired housing.

Suitable materials for housing the filter elements include materials having desired properties of one or more of the following mechanical strength, chemical resistance, weldability, material safety, and sterilization. Reference to "mechanical strength" means that the filter provides adequate structure to withstand at least a desired pressure rating and assembly of multiple capsules stacked on top of each other. Reference to "chemical resistance" means that the material does not degrade in the presence of chemicals in the incoming fluid including, but not limited to, one or more of the following: bases, alcohols, alkali. By "weldability," it is meant that the material will sealably adhere to itself and minimizes off-gassing and fuming upon welding by methods including, but not limited to, hot plate welding and ultrasonic welding. With respect to "material safety," it is expected that suitable materials will have extraction profiles suitable for pharmaceutical contact. In terms of "sterilization," a suitable material should be able to be sterilized without negative impact on the material by methods including, but not limited to, autoclave sterilization.

FIGS. 1A and 1B provide cross-sectional side views of different illustrative full-cell filter elements 100 comprising a media pack 9 and a separator element 49. The media pack 9 comprises two filtration medias 104, 104' and the separator element 49 is located between the two sides 15, 15'. The separator element 49 comprises a central hub 25 and support members 19 that together define passages 18. The support members may ribs, gussets, or any other structures that provide structural rigidity to the separator element 49. Each side 15, 15' and the separator element 49 are axially aligned. A periphery of each of inner edges 14, 14' is bonded directly to the separator element 49, for example at the central hub 25. The sides 15, 15' extend from the outer edge periphery 32 to the inner bond 106 at the inner edges 14, 14', respectively. In some embodiments, the media pack 9 may be a pocket-like extension of filtration media, for example, folded upon itself, not needing an outer bond.

An inner bond 106 affixes both filtration medias 104, 104' to a portion of the separator element 49 for example the central hub 25.

In the embodiment of FIG. 1A, an outer bond 108 among the layers of filtration media is formed at an outer edge periphery 32 of the filtration media 104, 104', where the layers are bonded to, in this example, each other. That is, the filtration media 104, 104' and/or the separator element 49 are sized such that the filtration media extends beyond the separator element 49, that is, the outer diameter (OD) of the filtration media 104, 104' is larger than that of the separator element 49. FIG. 2 shows a cross-sectional, enlarged side view of the outer bond 108 of FIG. 1. The outer bond 108 has a width "w." In one or more embodiments, the outer bond has a width that is in the range 50 mil to 250 mil from an outer edge of the filtration media.

In the embodiment of FIG. 1B, the configuration differs from that of FIG. 1A in that the separator element 49 and the sides 15, 15' have substantially the same outer diameter (OD). The outer edge periphery 32 of FIG. 1B may be bonded directly to the separator element 49, or it may be overmolded to form an overmold outer seal.

FIG. 3 is a cross-sectional side view of an illustrative media pack 9 having a first side 15 and a second side 15', the sides comprising two filtration medias 104 defining an interior 11. The two sides, 15 and 15' each have an inner surface 11B and an outer surface 11A. Each side may be multilayered. The filtration medias may have the same configuration or may be independently selected. In this embodiment, the two sides each comprise a layered filtration media which forms a media pack that is substantially flat. Other shaped-media packs may be chosen as desired. The inner surfaces 11B define an interior of the media pack.

The outer surface 11A of sides 15, 15' is the dirty-side or upstream side when fluid flow is from the exterior of a filter element or cell to interior 11; inner surface 11B is the filtered-side or downstream side of sides 15, 15'. When fluid flow is in the opposite direction, surface 11B would be the dirty-side or upstream side and surface 111A would be the filtered-side or downstream side.

FIG. 4 is a cross-sectional side view of an illustrative partial filter element, where partial filter element 99 has at least one media-containing portion in the form of filtration media 104. An inner bond 106 affixes an inner edge periphery of the filtration media 104 to a portion of separator element 49. In one or more embodiments, the inner bond has a width that is in the range 50 mil to 250 mil from the inner edge 14 of the filtration media 104. It is understood that for layered media, the layer adjacent to the separator element is being affixed directly to a portion of the separator element and that the layers above are affixed to each other, making the layers above indirectly affixed to the separator element. Nonetheless, in its simplest form, the inner bond is the direct connection between the separator element and the first adjacent layer. Depending on the needs of an application, the inner bond may comprise the collective connection of all of the layers to the separator element. An outer bond 108 affixes the outer edge periphery of the filtration media to, in this example, each other.

FIG. 5 is a cross-sectional side view of an illustrative half-cell filter element 101 wherein one side comprises two layers of filtration media 105a, 105b and the other side comprises a flow inhibitor 110, which covers and/or sealably affixes to the separator element 49 or to all or some portion of the filtration media 105a, 105b. The layer of filtration media 105a is bonded directly to separation element 49. An optional overmold inner seal 118 covers the inner bond 106 and inner edges of the flow inhibitor 110. A hub arrangement is formed by core 16 and the overmold inner seal 118. An optional ovemold outer seal 112 covers an outer edge periphery of the filtration media layers 105a, 105b and the flow inhibitor 110.

FIG. 6 is an exploded perspective schematic view of an illustrative layered filtration media 104 where each layer of media 116a, 116b, 116c, 116d, 116e, and 116f is independently chosen. In FIG. 6, layers 116a, 116b, 116d, and 116e are a first material, all the same material and 116e and 116f are both a second material, which is different from the first material. Each layer has an inner edge 14 and a central media opening 34. And each has an inner edge periphery 22 and an outer edge periphery 36.

Figure 7:
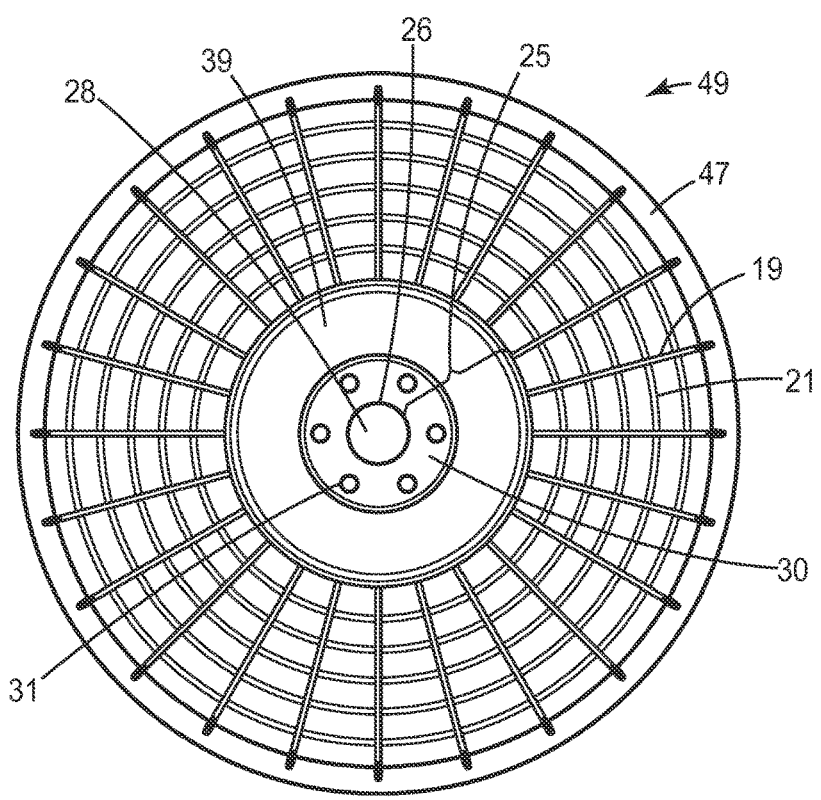
FIG. 7 is a top-view schematic of an exemplary separator element.

FIG. 7 is a top-view schematic of an exemplary separator element 49 comprising a central hub 25 defining a central separator opening 28, and a plurality of support members 19 that have an open structure. The open structure formed by the plurality of support members 19 may be intersected with further structure, such as with a series of concentric rings 21. The central hub 25 in this embodiment comprises a center ring 30 and a washer 39. The center ring 30 comprises an inner edge 26 and a plurality of through-holes 31. The washer 39 has a washer outer edge periphery. As needed, a center ring and a washer may be present on the underside of the separator element 49 for embodiments where both sides of the media pack are filtration media. When a flow inhibitor is used, a center ring and/or washer may not be needed. On its outer diameter (OD), the separator element comprises an outer lip 47.

Figure 8:
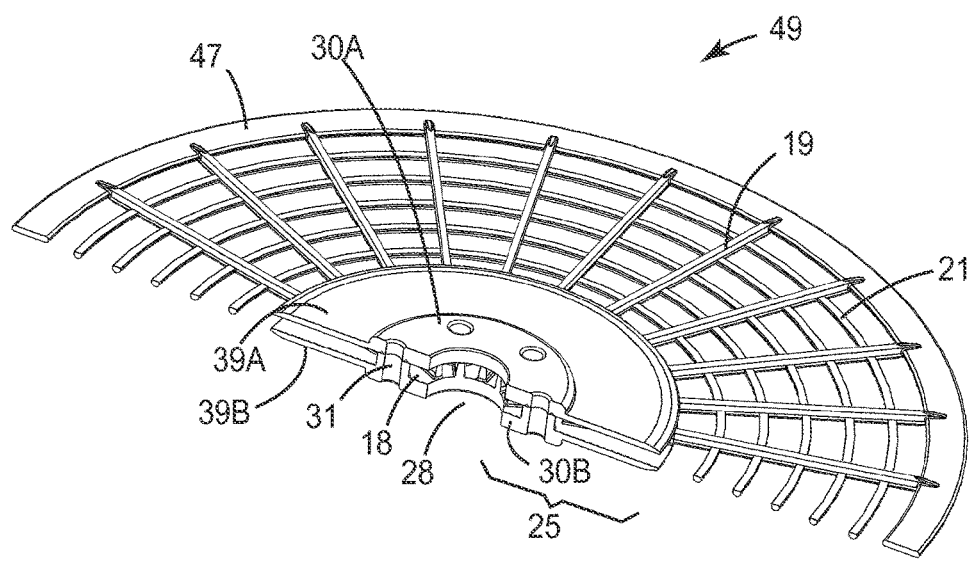
FIG. 8 is a cut-away view of the separator element of FIG. 7.

FIG. 8 is a cut-away view the exemplary separator element 49 of FIG. 7 showing two washers 39A and 39B and two center rings 30*a* and 30B, which form the central hub 25. A plurality of passages 18 are formed by the plurality of support members 19 and the central hub 25. When media is adjacent to the separator element 49, passages 18 provide fluid communication between the media and the central separator opening 28. Flow channels are formed in the spaces between the plurality of support members 19 and concentric rings 31.

Figure 9:
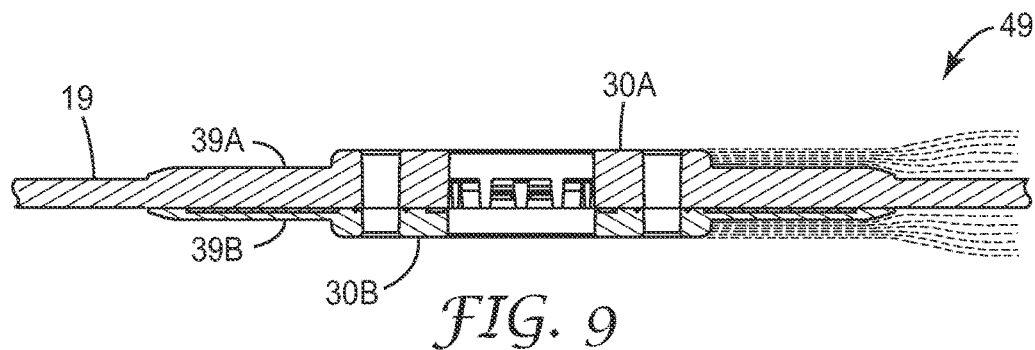
FIG. 9 is a schematic cross-sectional side view of the separator element of FIG. 7.

FIG. 9 is a schematic cross-sectional side view of the center of the separator element 49 of FIG. 7 showing the locations of center rings 30A and 30B and of washers 39A and 39B. It is understood that the center rings and/or washers may be integral to the open structure of the separator or they may be affixed to the separator and each other. Moreover, at least one center ring and at least one washer is needed. Thus, in some instances, the separator element 49 comprises one center ring and one washer, and in other instances, the separator element 49 comprises two center rings and two washers. The center rings 30A, 30B provide a structure that separates the edges 14 of the filtration media from being in communication with the central separator opening. For illustrative and non-limiting purposes, a close-up of a phantom of a portion of an inner bond is shown located on washers 39A and 39B and edges of the filtration media are not in communication with the central separator opening.

Figure 10:
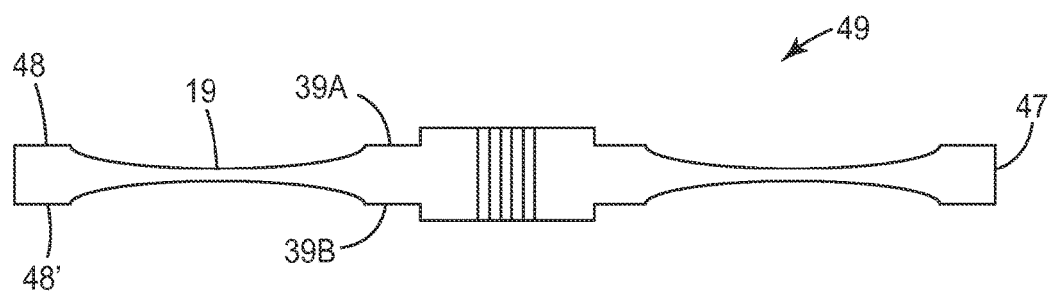
FIG. 10 is a perspective top view photograph of a portion of an exemplary full-cell filter element.

FIG. 10 is a schematic cross-sectional side view of the separator element 49 of FIG. 7 where the support member 19 and the outer lip 47 are shown along with washers 39A, 39B which are in the substantially same plane as the outer lip surfaces 48, 48', respectively. That is, relative to a horizontal center line of the support member 19, the surface 48 and the washer 39A are the same distance. Likewise, the surface 48' and the washer 39B are the same distance from a horizontal center line of the support member 19. The distances may be the same or different for each washer.

Figure 11:
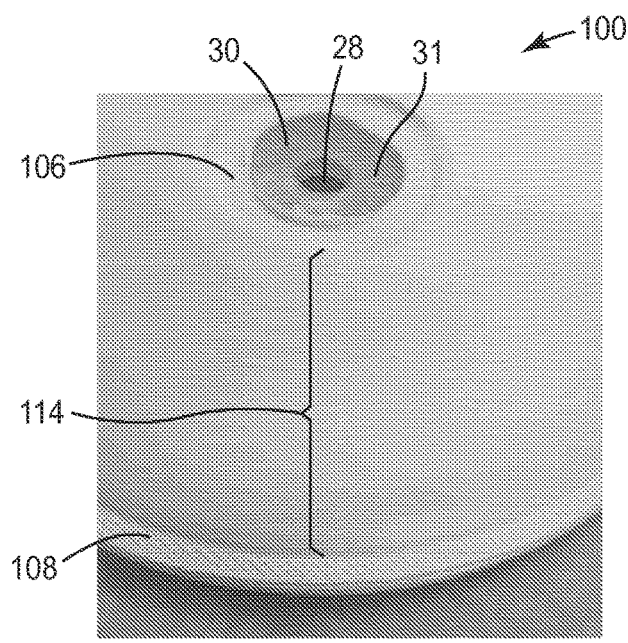
FIG. 11 is a schematic cross-sectional side view of the separator element of FIG. 9.

FIG. 11 is a perspective top view photograph of a portion of an exemplary full-cell filter element 100 showing a filtration area 114 of the filtration media (not numbered), the inner bond 106, and the outer bond 108. The center ring 30, through holes 31, and the central separator opening 28 of separator element are also shown.

Figure 12:
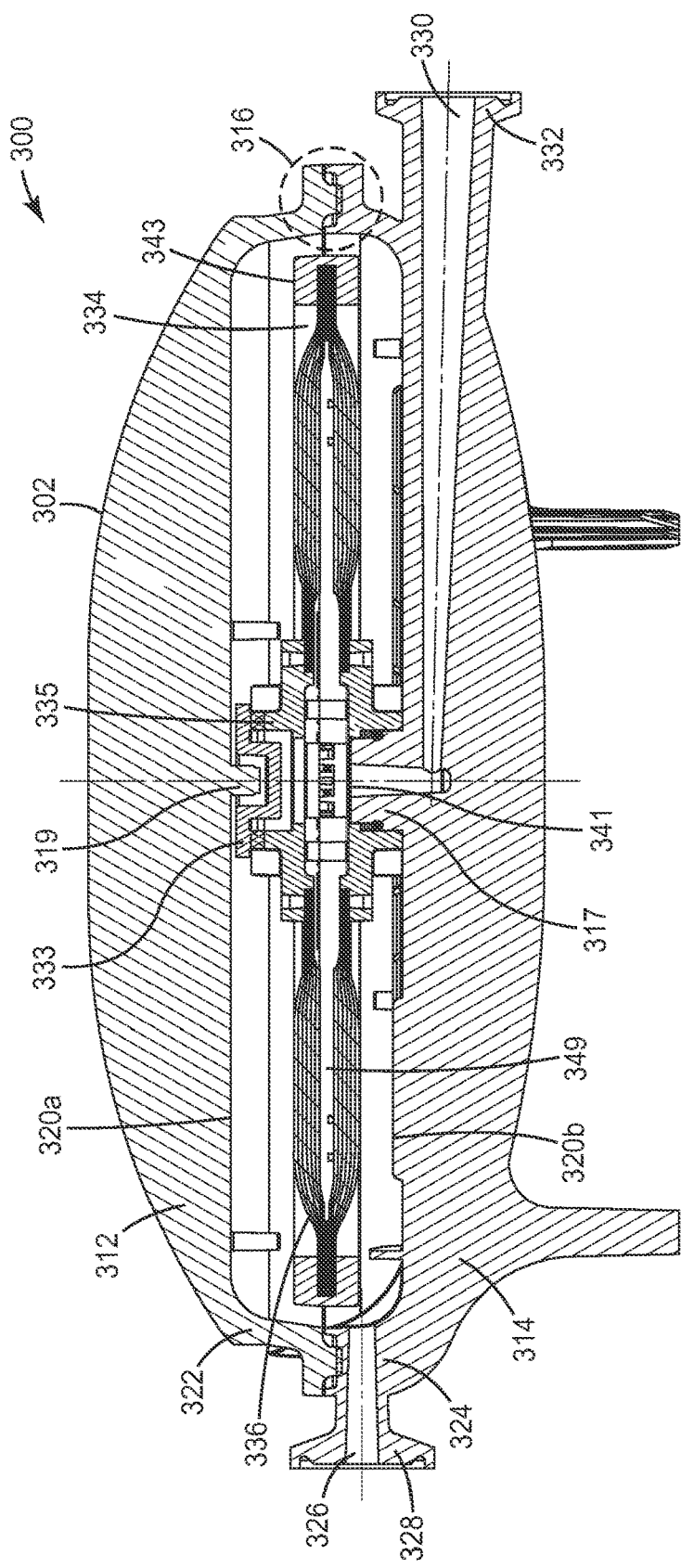
FIG. 12 is a schematic cross-sectional side-view of an illustrative filtration capsule.

FIG. 12 shows an exemplary filtration assembly or capsule 300, where its housing 302 is as disclosed in commonly-assigned WO2013/043362. The housing 302 comprises a first or top shell 312 and a second or bottom shell 314 that are sealably attached to each other via a vibration weld 316. The housing may have exterior surfaces that can be curved or domed or otherwise shaped to a desired configuration. The shells also each have substantially flat interior walls 320*a* and 320*b* that are integral to the shells 312 and 314, respectively. The presence of protrusions, such as 317 and/or 319, on the substantially flat interior walls 320*a* and 320*b* does not preclude these interior walls from being substantially flat. That is, there is no air-filled gap in the space between the flat interior walls and the curved exterior surface. When the two shells 312 and 314 are attached to each other, the area defined by the substantially flat interior walls 320*a*, 320*b* and sides 322, 324 is the capacity, which refers to the theoretical maximum volume of fluid that can be retained by a shell individually or the capsule as a whole in the absence of internal features. A filter element 336 according to any embodiment disclosed herein is located in the housing. The number of filter elements and their configuration may be chosen according to desired application and filtration capacity. Because of the presence of a filter element 336 and structures on the interior walls themselves, capacity is usually higher than what is referred to as the upstream volume, which is the amount of fluid required to fill the capsule. Hold-up or residual volume is that amount of fluid that remains (e.g., is held up) in the capsule after action to blow out the capsule upon reaching a certain endpoint such as plugging or a targeted pressure drop.

The second or bottom shell 314 also comprises an inlet 326 which may have a flange 328, and an outlet 330 that may also have a flange 332. For ease of construction, it is preferred that the inlet 326 and the outlet 330 are integral to the second or bottom shell 314. It is recognized, however, that the location of the inlet or the outlet or both may be moved to the first or top shell should such a need arise. The inlet 326 and outlet 330 are defined by respective passages through the shell structure and are substantially horizontal, that is substantially parallel to the substantially flat walls 320*a* and 320*b*. In use, attached to the flange 328 is a gauge, pipe, tubing, or the like that supplies an incoming fluid that contains particles or other contaminants to be removed by the filtration capsule 300. The fluid then enters the upstream volume 334 and contacts an outer surface (not numbered) of the filter element 336. In one or more embodiments, the filter element 336 is flat. Fluid passes through an outer surface of the filter element whose filtration media removes the particles and other contaminants from the incoming fluid. Filtration media may be a single layer or multiple layers.

After flowing through the filtration media, the fluid is then considered to be a filtered fluid which exits the filtration media from an inner surface that is in fluid communication with a core 341 and the outlet 330. A separator element 349 may be used to direct flow. In a specific embodiment, the separator element 349 has passages that direct the flow from the inner surface to the outlet 330 through the core 341. The filter element 336 has a direct bond to a portion of the separator element 349 and an optional overmold inner seal 335, which alone or in combination separates the filtered fluid from the incoming fluid. An optional overmold outer seal 343 may be used for further sealing and/or structural support. An endcap 333 also facilitates preventing bypass of the incoming fluid to the outlet 330. As desired, surface area available for filtration can be varied by the use of a flow inhibitor, which may covers and/or sealably affixes to the separator element 349 or to all or some portion of a media pack to prevent fluid from entering the filter element 336.

Before describing several exemplary embodiments of the invention, it is to be understood that the invention is not limited to the details of construction or process steps set forth in the following description. The invention is capable of other embodiments and of being practiced or being carried out in various ways.

EXAMPLES

Example 1

A filter element was made by placing inner diameter (ID) alignment fixtures on a Branson welder. A separator element was placed on a mandril. Two sets of filtration media layers were formed, the layers comprising, in order starting from the bottom or first layer: nonwoven material is polypropylene Typar, nylon 6,6 microporous membrane, and four layers of anion exchange (AEX) membrane. A first set of media was placed onto a first side of the separator element and axially aligned. To form a partial filter element, the ID was bonded using ultrasonic welding to form a first inner bond such that the Typar layer was adjacent to the separator element and the fourth AEX membrane formed the outer surface. The partial filter element was then flipped over and replaced on the mandril. A second set of media was placed onto a second side of the separator element and aligned. To form a full cell filter element, the ID was bonded using ultrasonic welding to form a second inner bond such that the Typar layer was adjacent to the separator element and the fourth AEX membrane formed the outer surface. The OD was then ultrasonically bonded to form an outer layer where all of the media layers were bonded together and not to the separator element. The filter element was then put into an injection molding machine where an overmold inner seal and an overmold outer seal were formed and this structure was put into a housing.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A filter element comprising:
a media pack comprising two sides each comprising: an inner edge having an inner edge periphery and an outer edge having an outer edge periphery, wherein at least one side comprises a filtration media comprising a microporous polymeric membrane;
a separator element located between the two sides, the separator element comprising a central hub defining a central separator opening and a plurality of support members extending from the central hub;
wherein at least one of the inner edge periphery and the outer edge periphery comprises a bond directly to a portion of the separator element and the at least one of the inner edge periphery and the outer edge periphery comprises an overmold seal over the bond.

2. The filter element of claim 1, wherein the bond is continuous thereby forming a hermetic seal.

3. The filter element of claim 1, wherein the bond comprises an adhesive or a polymer weld.

4. The filter element of claim 3, wherein the bond comprises a polymer weld selected from the group consisting of an ultrasonic weld, a high-frequency weld, a vibration weld, a friction weld, a laser weld, a solvent weld, a contact weld, a hot plate weld, a plastic rod weld, a speed tip weld, or a hot gas weld.

5. The filter element of claim 1, wherein the bond has a width that is in the range of 50 mil to 250 mil from at least one of the inner edge and the outer edge of the filtration media.

6. The filter element of claim 1, wherein the bond comprises an inner bond between the inner edge periphery of the filtration media and a surface of the central hub.

7. The filter element of claim 1, wherein the separator element comprises an outer lip, and a surface of a washer of the central hub and a surface of the outer lip are in the same plane.

8. The filter element of claim 1, wherein the bond comprises an outer bond between the outer edge periphery of the filtration media and the outer lip.

9. The filter element of claim 1, wherein the two sides of the media pack both comprise the filtration media.

10. The filter element of claim 9, wherein the bond comprises an outer bond between the filtration media.

11. The filter element of claim 1, wherein a first side of the media pack comprises the filtration media and a second side of the media pack comprises a flow inhibitor.

12. The filter element of claim 1, wherein the filtration media comprises a microporous membrane produced from a polymeric material.

13. The filter element of claim 1, wherein the filtration media comprises one or more layers of media.

14. The filter element of claim 13, wherein each layer comprises a thickness in the range of 5-40 mil.

15. The filter element of claim 13, wherein each layer independently comprises a polymeric material having a melting point in the range of 100° C. to 300° C.

16. A filter element comprising:
a media pack comprising two sides each comprising: an inner edge having an inner edge periphery and an outer edge having an outer edge periphery, wherein a first side comprises a first filtration media comprising a microporous polymeric membrane and a second side comprises a second filtration media or a flow inhibitor;

a separator element located between the two sides, the separator element comprising a central hub defining a central separator opening, a plurality of support members extending from the central hub, and an outer lip;

wherein the inner edge periphery of the first filtration media comprises an inner bond directly to the central hub; and wherein the outer edge periphery of the first filtration media comprises an outer bond directly to the outer lip of the separator; and wherein the inner edge periphery comprises an overmold seal over the inner bond.

17. The filter element of claim 16, wherein the first filtration media comprises two or more layers that are independently: a woven structure, a non-woven structure, a microporous membrane, a monolith, a melt-blown fiber (MBF) structure, or an open-cell foam formed from a material selected from the group consisting of: nylon, ethylene chlorotrifluoroethylene (ECTFE), polypropylene, polyethylene, polyvinylidene fluoride (PVDF), a polyethersulfone membrane, a polysulfone membrane, a polyester membrane, polytetrafluoroethylene (PTFE), polycarbonate, nitrocellulose, cellulose acetate, cellulose, or combinations thereof.

18. A method of integrity testing a filter element, the method comprising:
 obtaining a filter element of claim 16 wherein the inner bond and the outer bond are both continuous and wherein the filtration media may be wetted and dried without losing integrity;
 exposing an upstream side of the filter element to a test fluid to form an exposed element; and
 monitoring a downstream side of the filter element to detect leakage.

19. The method of claim 18, wherein the test fluid comprises a liquid, the method further comprising pressurizing the exposed element and the monitoring step comprises measuring pressure to detect leakage.

20. The method of claim 18, wherein the test fluid comprises a gas with particles entrained therein and the monitoring step comprises measuring a particle count to detect leakage.

21. A method of filtering, the method comprising:
 obtaining a filter element of claim 16 wherein the inner bond and the outer bond are both continuous;
 passing an incoming fluid through the filter element; and
 receiving a filtered fluid from the filter element.

22. A method of making a filter element, the method comprising:
 obtaining a first filtration media comprising a microporous polymeric membrane having a melting point in the range of 100 to 300 degree Celsius; an inner edge having an inner edge periphery and an outer edge having an outer edge periphery;
 locating a separator element on the first filtration media;
 axially aligning the first filtration media and the separator element;
 bonding at least one of the inner edge periphery and the outer edge periphery directly to the separator element to form a bond; and
 forming an overmold seal over the inner bond.

23. The method of claim 22, wherein the bonding step comprises ultrasonically welding the inner edge periphery to a washer of the separator element to form an inner bond and the outer edge periphery to itself or directly to an outer lip of the separator element to form an outer bond.

24. The method of claim 23 further comprising forming an overmold outer seal over the outer bond.

25. A filtration assembly comprising the filter element of claim 16 located in a housing.

26. A method of forming a filtration assembly, the method comprising: locating the filter element of claim 16 in a housing.

\* \* \* \* \*